United States Patent [19]

Bogerman et al.

[11] 4,242,219

[45] Dec. 30, 1980

[54] NOVEL ENZYME PARTICLES AND THEIR PREPARATION

[75] Inventors: Pieter K. Bogerman, Naaldwijk; Petrus J. Eygermans, Wateringen; Antoon G. van Velzen, The Hague, all of Netherlands

[73] Assignee: Gist-Brocades N.V., Delft, Netherlands

[21] Appl. No.: 919,082

[22] Filed: Jun. 26, 1978

[30] Foreign Application Priority Data

Jul. 20, 1977 [GB] United Kingdom .............. 30556/77

[51] Int. Cl.$^3$ .................. A61K 37/48; C11D 3/386; C12N 9/96; C12N 9/98

[52] U.S. Cl. .................. 252/174.12; 252/174.17; 252/174.25; 252/132; 252/DIG. 12; 424/35; 424/38; 424/94; 435/177; 435/178; 435/187; 435/188

[58] Field of Search .............. 252/89, 132, DIG. 12, 252/174.12; 195/62, 63, 66 R, 68; 435/177, 178, 187, 188; 424/94, 31, 32, 33, 35, 38

[56] References Cited

U.S. PATENT DOCUMENTS

| | | | |
|---|---|---|---|
| 3,072,532 | 1/1963 | Innerfield | 195/63 X |
| 3,519,570 | 7/1970 | McCarty | 252/135 |
| 3,661,786 | 5/1972 | Des Forges | 252/99 |
| 3,723,327 | 3/1973 | van Kampen | 252/110 |
| 3,775,331 | 11/1973 | Borrello | 252/89 |
| 3,853,780 | 10/1974 | Mostow | 252/132 |
| 3,868,336 | 2/1975 | Mazzola | 252/527 |
| 4,009,076 | 2/1977 | Green | 195/63 |
| 4,016,041 | 4/1977 | van Kampen | 195/68 |
| 4,106,991 | 8/1978 | Markussen | 435/187 |

FOREIGN PATENT DOCUMENTS

| | | | |
|---|---|---|---|
| 1204123 | 9/1970 | United Kingdom | 252/106 |
| 1362365 | 8/1974 | United Kingdom . | |
| 1509866 | 5/1978 | United Kingdom . | |

*Primary Examiner*—Dennis L. Albrecht

[57] ABSTRACT

A novel process for preparing non-dusting, enzyme-containing particles, e.g. for introduction into washing compositions, comprising homogeneously mixing an amount of an enzyme in dry or substantially dry form to give the desired enzyme activity in the particles when formed, about 20% to about 60% of a hydrophilic organic cohesive compatible with the enzyme, about 10% to about 60% of a building agent suitable for use in enzyme compositions, and a sufficient amount of water, if necessary, to give a moisture content in the particles, when formed, of from 5% to 15%, mechanically dividing the mixture obtained into particles of the desired size, and coating the particles to prevent loss of moisture and the novel enzyme particles produced thereby as well as washing compositions and pharmaceutical compositions containing said enzyme particles.

33 Claims, No Drawings

NOVEL ENZYME PARTICLES AND THEIR PREPARATION

STATE OF THE ART

Enzymes have been used in washing compositions for several years but one of the problems in the formulation of enzymatically active washing compositions is the fact that, when formulating the enzymatic washing compositions enzyme dust is formed. This is disagreeable to the people working with the enzyme compositions and sometimes, skin irritations or allergic reactions occur.

Dusting of the enzyme may be avoided to a considerable extent by changing the enzyme into a form other than a powder in which it is normally obtained and this is advantageously done by converting the enzyme into a solid particulate form. Processess for changing enzymes into a particulate form are known, for example, as described in British Pat. No. 1,324,116 which discloses a process wherein a liquid mixture of the enzyme and a binder such as a low-melting nonionic emulsifier is dispersed into droplets by a toothed disc, and is guided into a cooling tower wherein the droplets are allowed to solidify. In this manner, a dust-free product is obtained, which is easily formulated into washing compositions.

Although the enzyme particles obtained according to the said British patent are good and may be used without risk of dust formation, they have shown the disadvantage that, if mechanical pressure is exerted upon the particles, e.g. the foot pressure of somebody walking over spilled particles, they easily break down into smaller particles and powder so that enzyme powder from the broken particles may be carried among with air currents.

OBJECTS OF THE INVENTION

It is an object of the present invention to provide pliant enzyme particles that do not, or substantially do not, break down to powder when mechanical pressure is applied to them.

It is a further object of the invention to provide washing and pharmaceutical compositions containing dust-free, enzyme containing particles.

It is another object of the invention to provide a novel process for the preparation of dust-free, enzyme containing particles which are resistant to mechanical breakage.

These and other objects and advantages of the invention will become obvious from the following detailed description.

THE INVENTION

The novel process of the invention for the preparation of enzyme-containing particles which do not, or substantially do not, dust when external mechanical pressure is applied to them comprises homogeneously mixing an amount (preferably up to about 50%) of an enzyme in dry or substantially dry form sufficient to give the desired enzyme activity in the particles when formed, about 20 to about 60%, (preferably about 30% to about 50%) of a hydrophilic organic cohesive compatible with the enzyme, about 10% to about 60% (preferably about 20% to about 45%) of a building agent suitable for use in enzyme compositions, and a small amount of water, if necessary, sufficient to give a moisture content in the final particles when formed of from 5% to 15%, mechanically dividing the mixture obtained into particles such as pellets, of desired size, and coating the particles so as to prevent loss of moisture.

It may not be necessary to add water if the moisture content of the components is sufficient to supply the required moisture content in the final product. There may optionally be added an amount of a moisture-regulating agent sufficient to maintain a moisture content in the particles when formed of from about 5% to about 15% at ordinary temperatures and ordinary relative humidities.

The percentage mentioned in this specification and the accompanying claims are percentages by weight, unless otherwise indicated.

For the washing compositions of the invention, the basic formulation may be selected from a wide range of raw materials since they need not be consumable, although they preferably are biodegradable. For pharmaceutical compositions destined to be administered orally, the components should be edible and pharmaceutically-acceptable.

The enzyme-containing particles obtained by the invention are extremely useful for washing compositions if, for the purpose, the enzymes are selected from those customarily used in washing compositions. Examples of these enzymes are proteolytic enzymes (proteases), amylolytic enzymes (amylases), or lipolytic enzymes (lipases) and mixtures thereof. Examples of suitable proteolytic enzymes are enzymes from bacterial origin, such as proteolytic enzymes from Bacillus species, e.g. *B. subtilis, B. licheniformis* and *B. alcalophilus.* Amylolytic enzymes are preferably also enzymes of bacterial origin, such as amylolytic enzymes produced by Bacillus species, e.g. *B. subtilis.* Some bacteria produce suitable proteolytic and amylolytic enzymes simultaneously. Lipolytic enzymes which may be used are preferably also enzymes of microbial origin. They may be produced by Candida species, e.g. *Candida cylindraceae.* Lactases are also useful. Enzymes useful for pharmaceutical compositions are, e.g. invertase, glucoamylase etc.

The hydrophilic organic cohesive used in the formation of th enzyme mix may be selected from starch and cellulose derivatives, and a preferred type of starch derivative is acetylated amylopectin called "amylopectin gum". This type of gum is an amylopectin with an acetylation degree of about 5% to about 30%. Examples of other useful cohesives are gum arabic, dextrin, karaya gum, methylcellulose, tragacanth and other types of amylopectin, such as methylamylopectin. Certain starch hydrolysates preferably having a DE (Dextrose Equivalent) of about 30 may also be used. A starch hydrolysate may be used as cohesive if it has cohesive properties, i.e. if it contains amylopectin derivatives.

The building agent included in the enzyme mix is preferably a water-soluble carbohydrate, generally containing from 5 to 12 (preferably 6) carbon atoms. Suitable examples of carbohydrates having 5 carbon atoms—the pentoses are xylose, arabinose, ribose and lyxose. Suitable examples of carbohydrates having 6 carbon atoms (the hexoses) are glucose, mannose, galactose, fructose and sorbose. Furthermore, disaccharides, normally having 12 carbon atoms, may be used, such as sucrose, maltose, or cellobiose. The most preferred carbohydrate is glucose. As glucose crystallizes rather easily as do several other carbohydrates, a part, or all of the glucose or other carbohydrate may be replaced by starch hydrolyzed to a certain extent. A starch hydrolysate of about 20 to about 70 DE, preferably about 30 to about 60 DE, is advantageously used. These starch hydrolysates are also called glucose syrups. Preferably, an amount of about 40% to about 70% of the total weight of the builder is used to replace the glucose or other carbohydrate with the preferred building agents being glucose, sucrose and starch hydrolysate. It will be appreciated that starch hydrolysates having cohesive properties may exert a two-fold action, as cohesive agent and building agent.

Lubricating agents can be added to the enzyme mix to facilitate the mixture of components being divided into particles by mechanical means. Preferably, about 2% to about 7% (advantageously about 3% to about 5%) of lubricating agent is added to the enzyme mix. Examples of lubricating agents which may be used according to the invention are polymeric substances such as polyvinyl alcohol, paraffin oil or wax, stearic acid, and polyvinylpyrrolidone and glycerol also act as a lubricating agent.

A moisture-regulating agent may be included in the enzyme mix in an amount sufficient to maintain a desired moisture content. It is necessary to maintain a total moisture content of about 5% to about 15%, preferably about 5% to about 10%, to maintain the pliant nature of the enzyme particles after their formation. Examples of agents useful to maintain the moisture content are polyols of 2 to 6 carbon atoms and b 2 to 4 hydroxy groups attached to different carbon atoms. Examples of such compounds are ethyleneglycol, 1,2- and 1,3-propyleneglycol, 1,2-, 1,3- and 2,2-butyleneglycol, glycerol and sorbitol. Glycerol and sorbitol are preferably used. To maintain the above-indicated moisture content, about 0.5% to about 5%, preferably about 1% to about 3%, of the moisture-regulating component is added, depending on the circumstances.

Furthermore, other ingredients may be added to the enzyme mixture before forming particles therefrom, for example a pigment such as titanium dioxide or an optical brightener. The amounts normally used are about 1% to about 10%, preferably about 3% to about 7%, of pigment, especially in the case of titanium dioxide. Moreover, fillers may be added, such as silica, Penicillium mycelium, cellulose-containing powder or fibers, sawdust and bentonite, in amounts of, for example, 3% to 10%. The fillers may be added for the purpose of structural stability of the particles, especially when the compositions are to be handled in large quantities.

The ingredients may be mixed together in any sequence at ambient temperature or even at elevated temperatures, with the maximum temperature being dependent on the nature of the enzyme. The mixture is a powder at normal temperatures but becomes plastic at elevated temperatures and upon application of pressure. The lower temperature to be applied may be that at which the mixture just becomes plastic and the higher temperature is dependent on the nature of the enzyme. Temperatures of about 40° to about 70° C. are generally suitable, although in particular cases other temperatures may, or must, be employed. The plastification of the mixture can be effected by a kneader-mix, and in principle any mixer may be used in which the mixture is plastified under mild conditions (at low shear), and from which the plastified mixture may be taken off, batchwise or continuously.

Directly after plastification, the still plastic mixture is pressed through a pump and string-forming apparatus, for example a gear pump and an extruder. The string-forming apparatus may comprise a single- or multihole die plate, through which strings of desired cross-sections may be formed, e.g. cross-section of about 0.5 to about 3 mm, preferably 0.7 to 1.5 mm.

The desired particles may be obtained in granulated form by cutting up the strings formed. Granulating equipment for that purpose may be located at some distance from the die plate. Granulation may also be effected by cutting equipment provided with one or more moving edges cutting the extruded product on the die plate. The cutting equipment is preferably composed of a number of rotating knives arranged in such a manner that the knives, depending on the location of the rotation axis with respect to the die plate, move either continuously, or once per rotation, across the die plate.

It is also possible to combine the plastification, pumping and granulating steps in one piece of equipment, e.g. a screw extruder. The hopper of the extruder is filled with the powdery mixture, which, when fed to the equipment, is rendered plastic by the heat and pressure generated by the rotating screw. The last part of the screw effects a mixing action and pressure generation sufficient for extrusion through a multi-orifice die plate. The components of the mixture, in the desired ratio, may also be supplied separately to suitable equipment combining mixing, plastification, pumping and extrusion through a die plate. An example of such equipment is a double screw extruder provided with mixing facilities.

Depending on the desired size of the enzyme particles, a plate having orifices of about 0.5 to about 3 mm, preferably 0.7 to 1.5 mm, is used, although larger or smaller orifices may be used in particular cases. The size and also the shape of the enzyme particles depend also on the speed of the cutting knives, their number and the composition of the mixture.

To avoid loss of moisture, the resulting particles are coated, preferably with about 0.5% to about 5% depending on the type of coating agent of a coating which may be selected from e.g. a number of water repellent agents, such as paraffin oil or linseed oil, several types of waxes such as earth wax, cocoa fat, candelilla wax, carnauba wax, ceresine wax, lanolin, paraffin wax, beeswax and mixtures thereof. Agglomeration of the particles, which may occur when they are put into bags for transport, may be avoided by further coating of the particles already coated as described above, with an anti-caking agent such as corn starch or other starches, absorbing silicas, such as Aerosil, or talcum powder.

The enzyme-containing particles obtained by the invention do not, or substantially do not, cause enzyme dust formation. The formation of enzyme dust may be measured by a standard test method such as the elutriation test which is described in Belgian Pat. No. 838,125 and is carried out with a sample of 60 grams. The activity of the dust is measured, in the case of a protease, in DU (Delft Units, method described in British Pat. No. 1,353,317, page 4 line 114 et seq.). The dust formation, measured according to the elutriation test, is for particles of the invention below about 100 DU, preferably below about 50 DU.

The invention furthermore relates to enzyme particles prepared by the process indicated hereinbefore. Depending on the conditions under which the particles have been prepared, they may, for the purpose of washing compositions, have particle sizes of about 0.2 to about 3 mm, preferably about 0.5 to about 1.5 mm, in cross-section. For other purposes, e.g. for pharmaceutical compositions administered orally, the particle sizes will usually, as in normal practice, be greater. The particles are pliant in nature and may be deformed under pressure without breaking down to powder nad causing dust formation in this way. Pressure, however, as occurring in bags filled with the particles, should not deform the particle excessively. The "pliability" of the particles may be adapted for different bag sizes. In small bags, the pressure on the particles in the lower regions of the bags is smaller than in large bags, and for small bags, the requirements as to resistance to deformation are less stringent than for large bags.

The invention also relates to washing compositions containing, in addition to the usual washing composition components, the enzyme-containing particles prepared by the process. These washing compositions furthermore contain one or more detergents which are commonly used in enzymatic washing compositions, such as nonionic and anionic detergents, e.g. sodium benzenesulfonate. The washing compositions normally contain agents which inter alia have a softening effect on the washing water such as complex phosphates, e.g. sodium tripolyphosphate, sodium pyrophosphate, or phosphate-free water softeners, e.g. nitrilotriacetic acid or its salts, or sodium citrate. Other components may be added, e.g. anhydrous sodium silicate, weak alkaline components such as sodium bicarbonate, oxidizing agents such as sodium perborate, fillers such as sodium sulfate and other components such as carboxymethylcellulose, perfumes, optical brighteners and pigments such as titanium dioxide.

Usually, an amount of enzyme particles prepared by treatment of the invention of a proteolytic enzyme is employed to give the final washing composition a proteolytic activity of about 1000 to about 3000, preferably about 1500 to about 2500, DU/g. The amount of detergent used in the washing composition is generally about 4% to about 20%, preferably about 6% to about 12%. The amount of water-softening agent is generally about 35% to about 55%, preferably about 40% to about 50%. The amount of the remaining components is generally about 1% to about 20%, the filler making up the 100%. The preparation of the washing composition is carried out in the usual way. All ingredients may just be mixed together, or a master-batch is prepared first containing some of the ingredients to be added in low percentages.

The present invention also includes within its scope enzyme compositions hereinbefore described suitable for forming enzyme-containing particles by the process of the invention before plasticization.

In the following examples there are described several preferred embodiments to illustrate the invention. However, it should be understood that the invention is not intended to be limited to the specific embodiments.

EXAMPLE 1

A mixture of 1 part by weight of glycerol, 2 parts by weight of polyvinylpyrrolidone and 2 parts by weight of Berol 80 (ethoxylated $C_{18}$ fatty alcohol containing about 80 ethyleneoxide units) was heated until dissolution occurred and the solution was then added to 26 parts by weight of a Maxatase concentrate (commercial enzyme) of about 1.7 MDU/g. Then, 5 parts by weight of titanium dioxide, 15 parts by weight of glucose syrup (starch hydrolysate of about 43 DE), 15 parts by weight of glucose, 33 parts by weight of Amylogum CLS-0473 (an acetylated amyopectin from Avebe, Holland), and about 1 part by weight of water were added thereto and the total moisture content of the resulting mixture was about 7%. The mixture was mixed to a homogeneous paste at a temperature of about 65° C. and was fed to an extruder provided with a perforated plate having orifices of 1 mm. The extruder was further provided with two rotating cutting knives just behind the perforated plate, and with a jacket fed with cooling or heating water, as desired. The paste was extruded at a temperature of about 65° C. and the extruded strings were immediately cut into small particles by the cutting knives. The particles were cooled in a tray and the thus-obtained particles, having cross-sections of about 2 mm and having a (calculated) proteolytic activity of 0.43 MDU/g were coated with 1% by weight of paraffin oil, followed by 3% of corn starch. The enzyme-containing particles thus obtained were deformable under mechanical pressure without disintegration, but under the normal pressure occurring in the lower parts of commonly used bags the particles were hardly deformed for more than a few percent. The elutriation test showed a value of 18 DU.

Formulation into a washing composition

The thus obtained particles were used for the formulation of a washing composition. The following ingredients were mixed together: 54 parts by weight of sodium sulfate, 24 parts by weight of sodium tripolyphosphate, 6 parts by weight of sodium pyrophosphate, 10 parts by weight of sodium bicarbonate, 2 parts by weight of sodium carboxymethylcellulose, and 4 parts by weight of a dialkylphenoxypoly-(ethylene)ethanol. After mixing the ingredients intimately to form a washing composition, 0.5 parts by weight of the enzyme-containing particles [prepared as indicated above] were added and were intimately mixed throughout the washing composition. The washing composition thus obtained had the same washing activity as a similar washing composition in which the enzyme-containing particles were replaced by an amount of the enzyme particles obtained according to the process indicated in British Pat. No. 1,324,116 having the same enzymatic activity in the final washing composition (about 2000 DU/g).

EXAMPLE 2

Preparation of enzyme-containing particles with varying amounts of fillers and various coatings Starting from the recipe indicated in Example 1 for the enzyme-containing particles, the following fillers and coatings were used in the amounts stated:

| Filler | Coating 1 | Coating 2 | Elutriation test (DU) |
|---|---|---|---|
| 5% C | 0.5% E | 3% G | 45 |
| 2% A | 2.5% E + 2.5% F | 2% A | 32 |
| 2% A | 2.5% E + 2.5% F | 3% G | 18 |
| 2% A | 0.5% E + 0.5% F | 1% A | 10 |
| 1% A | — | 1% A | 80 |

A = Aerosil 972 (a hydrophobic silica adsorbent)
C = Arbocel C250 (a fine saw-dust)
D = Bentonite
E = Paraffin oil
F = Glycerol monostearate
G = Corn starch The above Table shows that all enzyme-containing particles prepared have rather low elutriation values, with the most preferred being the fourth sample. The enzyme particles were formulated into washing compositions in the manner indicated in Example 1 and the washing compositions showed the same washing activity as a similar washing composition containing the enzyme particle according to British Pat. No. 1,324,116.

The elutriation test mentioned above is carried out as follows: A bed of enzyme particles was exposed to an air stream so that the particles having a predetermined final speed or lower were taken along by the air stream. The method is a modification of the standard elutriation test described in BS 3406, Volume 3, 1963, and was carried out in a vertically arranged elutriation tube containing a dust filter. The particles taken along were collected on the filter and weighed, and their enzymatic activity was determined (expressed in glycine units or Delft units). The mean air current speed was 0.8 m/sec.

EXAMPLE 3

Preparation of enzyme-containing particles with varying amounts of fillers

Starting from the recipe indicated in Example 1 for the enzyme-containing particles, the following fillers were used: 2% of Aerosil 972; 5% and 10% of bentonite; and 5% of penicillin mycelium (obtained from the fermentation broth resulting from penicillin-G fermentations). The particles were coated with 1% of paraffin oil followed by 1% of Aerosil 972. All fillers indicated turned out to be useful, although the particles containing 10% of bentonite tended to be a little brittle.

The enzyme particles were formulated into washing compositions in the manner indicated in Example 1 and the washing compositions showed the same washing activity as a similar washing composition containing the enzyme particles of British Pat. No. 1,324,116.

EXAMPLE 4

The preparation of the particles of Example 1 was repeated except that Amylogum CLS-0473 was replaced by an equal amount of Paselli MD-30 (a starch hydrolysate having a DE of about 30). The particles were coated with 1% of paraffin oil followed by 1% of Aerosil 972.

According to another experiment, the preparation of particles were repeated according to Example 1 except that the Berol-80, the polyvinylpyrrolidone and the glucose were excluded and replaced by 10 parts by weight of bentonite. All components were admixed together at a temperature of about 65° C. and the resulting paste was extruded and cut into particles. The particles were coated in the same way as for the particles containing the Paselli MD-30.

The particles of both preparations of this Example were found to be very useful, and formulations of washing compositions [prepared in the same manner as in Example 1] showed substantially the same washing activity as a similar washing composition containing enzyme particles of British Pat. No. 1,324,116.

EXAMPLE 5

Preparation of enzyme-containing particles for pharmaceutical use

The following recipe was used for the preparation of a granulate according to the invention: 25% of glucoamylase (about 25,000 U/g), 6.25% of invertase (about 325,000 SU/g), 45% of Amylogum CLS-0473, 20% of glucose syrup (starch hydrolysate of about 43 DE), and 3.75% of glycerol. The powder was directly extruded through orifices of 1 mm diameter and the extrudate was cut to form granules. The granules were coated as described in Example 1. This type of preparation was useful for oral administration to patients suffering from an impaired carbohydrate metabolism caused by a deficiency of invertase, glucoamylase or isomaltase.

EXAMPLE 6

The following recipe was used for detergent formulation; 50% of Maxatase (2.3 million DU/g), 35% of Amylogum CLS-0473 and 15% of glucose syrup (starch hydrolysate about 43 DE). This recipe was formed into granules as indicated in Example 5 and after granulation, the particles were coated with 5% of titanium dioxide.

EXAMPLE 7

The following recipe was prepared for detergent formulation: 45% of methylcellulose, 20% of Maxatase (2.4 million DU/g), 10% of glucose syrup (starch hydrolysate,about 43 DE), 4% of paraffin wax, 5% of titanium dioxide, 2% of glycerol and 14% of glucose. A granulate was made according to the method described in Example 5 with coating of the granulate carried out as described in Example 3. The granules proved to have similar properties to those of Example 5.

EXAMPLE 8

The following recipe was prepared: 45% of gum arabic, 20% of Maxatase (2.4 million DU/g), 10% of glucose syrup (starch hydrolysate, about 43 DE), 4% of paraffin wax, 5% of titanium dioxide, 2% of glycerol and 14% of glucose. A granulate was prepared by the method described in Example 5 with coating of the granules carried out as described in Example 3. The granules proved to have similar properties.

EXAMPLE 9

A preparation containing amylase

The following recipe was prepared: 25% of amylase (16,400 BAU/g), 37% of Amylogum CLS-0473, 16% of glucose syrup (starch hydrolysate, about 43 DE), 16% of glucose, 5% of titanium dioxide and 1% of glycerol.

Another recipe was also prepared: 50% of amylase (16,000 BAU/g), 35% of Amylogum CLS-0473 and 15% of glucose syrup (starch hydrolysate, about 43 DE). A granulate was made of each of the recipes by the method described in EXAMPLE 5 with coating of the granules carried out as described in Example 3. Both proved to have similar properties.

EXAMPLE 10

Using the procedure of Example 5, other properties were made as reported in the following Table and the particles were coated as in Example 3.

| Ingredients | Sample Number | | | | | | |
|---|---|---|---|---|---|---|---|
| | 1 | 2 | 3 | 4 | 5 | 6 | 7 |
| Amylogum CLS-0473 (%) | 40 | 40 | 40 | 40 | 40 | 40 | 40 |
| Maxatase (%)(1) | 20 | 20 | 20 | 20 | 20 | 20 | 20 |
| sorbitol (%) | — | 2 | — | — | — | — | — |
| glycerol (%) | 2 | — | 2 | 2 | 2 | 2 | 2 |
| paraffin wax (%) | — | — | 4 | — | 2 | 4 | 4 |
| Aerosil 972 (%) | — | — | — | 2 | 1 | — | — |
| Berol 80 (%) | 1 | 1 | 1 | 1 | 1 | — | — |
| titanium dioxide (%) | 5 | 5 | 5 | 5 | 5 | 5 | 5 |
| glucose (%) | 22 | 22 | 18 | 20 | 19 | 19 | 14 |
| glucose syrup (%)(2) | 10 | 10 | 10 | 10 | 10 | 10 | 10 |

-continued

| Ingredients | Sample Number | | | | | | |
|---|---|---|---|---|---|---|---|
| | 1 | 2 | 3 | 4 | 5 | 6 | 7 |
| Elutriation test (3) | 29 | 20 | 14 | 10 | 20 | 32 | 11 |

(1) 2.18 million DU/g
(2) starch hydrolysate, about 43 DE
(3) for 60 grams of sample The said granules had good properties.

EXAMPLE 11

The following recipe containing an alkaline protease was prepared: 34% Amylogum CLS-0473, 17% of glucose, 17% of glucose syrup (starch hydrolysate, about 43 DE), 7% of stearic acid, 20% of PB 92 (1.7 million ADU/g) (1) and 5% of titanium dioxide.

A granulate was made by the method of Example 5 with coating of the granulate carried out as in Example 3. The granulate proved to have similar properties: inter alia the elutriation test applied on a sample of 60 g showed a value of 95 ADU/g. (1) PB 92 is an alkaline proteolytic enzyme described in U.S. Pat. No. 4,002,572.

EXAMPLE 12

Storage stability of the granulate 400 g of a commercially available washing powder containing sodium perborate were added to an amount of enzyme granulate of Example 10 (Sample 5) previously coated with 1% of a 1:1 mixture of glycerol monostearate and paraffin oil, to make the activity 6,000 DU/g and the composition was mixed thoroughly again. Weighed samples of about 20 g taken from the mixture were analyzed for a storage stability test just after mixing and after 0.5, 1, 2 and 3 months storage at 37° C. The samples were tested by dissolving them in synthetic tap water (containing 111 mg/l of CaO, 27.5 mg/l of MgO and 210 mg/l of NaHCO$_3$, German Hardness 15° ), containing sufficient sodium dithionite to neutralize the action of the perborate, and diluting with synthetic tap water to a concentration suitable for testing the activity in Delft Units (cf. British Pat. No. 1,353,317) (series A in the following Table).

A similar test was run with a commercially available granulate of the same enzyme (Maxatase P. prepared by the method described in British Pat. No. 1,324,116) (series B.). The following results were obtained:

| Storage time (in months) | 0.5 | 1 | 2 | 3 |
|---|---|---|---|---|
| Series A | 100 | 99 | 89 | 91 |
| Series B | 94 | 92 | 82 | 75 |

The Table shows that the storage stability of series A of the invention is good and is even better than that of the comparative series B, which also had a fairly good stability.

EXAMPLE 13

A preparation containing lactase was prepared as follows: 45% of Amylogum CLS-0473, 30% of lactase (precipitated) and 25% of glucose syrup (starch hydrolysate, about 43 DE). A granulate was made by the method of Example 5 and was coated as described in Example 3. When the temperature was kept at 50° C. or below during preparation of the granules, the activity of the granulate was 95% of the starting activity, whereas, when the temperature was allowed to rise to 50° to 70° C. the remaining activity was considerably lower, i.e. 55% of the original activity. This Example shows that the temperature to be used depends greatly on the enzyme.

EXAMPLE 14

The following recipe was used for the preparation of particles by the procedure described in Example 1: 1 part by weight of glycerol, 2 parts by weight of polyvinylpyrrolidone, 2 parts by weight of Berol 80, 1 part by weight of Maxatase, 5 parts by weight of titanium dioxide, 22 parts by weight of glucose syrup (starch hydrolysate of about 43 DE), 21 parts by weight of glucose and 46 parts by weight of Amylogum CLS-0473. The particles were coated as described in Example 1.

Various modifications of the products and process of the invention may be made without departing from the spirit or scope thereof and it should be understood that the invention is intended to be limited only as defined in the appended claims.

What we claim is:

1. A process for the preparation of enzyme-containing particles which do not, or substantially do not, dust when subjected to external mechanical pressure comprising homogeneously mixing an amount of an enzyme in dry or substantially dry form sufficient to give the desired enzyme activity in the particles when formed, about 20% to about 60% of a hydrophilic organic cohesive compatible with the enzyme selected from the group consisting of starch derivatives, cellulose derivatives, arabic gum, karaya gum and tragacanth, about 10% to about 60% of a building agent suitable for use in enzyme compositions selected from the group consisting of water-soluble carbohydrates of 5 to 12 carbon atoms, up to 70% of which may be replaced by a starch hydrolysate of about 20 to about 70 DE, and an amount of a moisture regulating agent selected from the group consisting of polyols having 2 to 6 carbon atoms and 2 to 4 hydroxy groups attached to different carbon atoms sufficient to maintain a moisture content in the particles formed of from 5% to 15% at ordinary temperatures and ordinary relative humidities and sufficient water to give a moisture content in the particles formed of from 5% to 15%, mechanically dividing the mixture obtained into particles of the desired size, and coating the particles to prevent loss of moisture with about 0.5 to about 5% of a water repellent agent selected from the group consisting of paraffin oil, linseed oil, earth wax, cocoa fat, candelilla wax, carnauba wax, paraffin wax and beeswax, ceresine wax and lanolin and mixtures thereof.

2. The process of claim 1 wherein the composition contains up to 50% of the enzyme and 20 to 60% of the building agent.

3. The process of claim 1 wherein the hydrophilic cohesive is selected from the group consisting of acetylated amylopectin, gum arabic, dextrin, karaya gum, methylcellulose, tragacanth, methylamylopectin and starch hydrolysates having cohesive properties.

4. The process of claim 1 wherein the hydrophilic cohesive is acetylated amylopectin with an acetylation degree of about 5 to about 30%.

5. The process of claim 1 wherein the amount of hydrophilic cohesive used is about 30% to about 50%.

6. The process of claim 1 wherein the building agent is selected from the group consisting of water-soluble carbohydrates containing 5 to 12 carbon atoms.

7. The process of claim 1 wherein the building agent is selected from the group consisting of glucose, sucrose and starch hydrolysate.

8. The process of claim 1 wherein the building agent is a mixture of glucose and 40 to 70% of starch hydrolysates having a Dextrose Equivalent of about 20 to about 70.

9. The process of claim 8 wherein the Dextrose Equivalent of the starch hydrolysate is about 30 to about 60.

10. The process of claim 1 wherein the amount of building agent used is about 20 to about 45%.

11. The process of claim 2 wherein the moisture regulating agent is selected from the group consisting of glycerol and sorbitol.

12. The process of claim 2 wherein the amount of moisture regulating agent used is about 0.5 to about 5%.

13. The process of claim 12 wherein the amount of moisture regulating agent is about 1 to about 3%.

14. The process of claim 1 wherein the enzyme is selected from the group consisting of proteases, amylases, lipases, lactases, invertase, and glucoamylase.

15. The process of claim 14 wherein the proteases are selected from those produced by Bacillus strains.

16. The process of claim 15 wherein the Bacillus strain is selected from the group consisting of *Bacillus subtilis, Bacillus licheniformis* or *Bacillus alcalophilus*.

17. The process of claim 14 wherein the amylase is selected from those produced by *Bacillus subtilis*.

18. The process of claim 14 wherein the lipase is selected from those produced by Candida strains.

19. The process of claim 18 wherein the Candida strain is *Candida cylindraceae*.

20. The process of claim 14 wherein the amount of enzyme used is up to about 50%.

21. The process of claim 1 wherein additionally 2 to 7% by weight of a lubricating agent selected from the group consisting of paraffin oil or wax, stearic acid, polyvinyl alcohol, polyvinylpyrrolidone and glycerol is added.

22. The process of claim 21 wherein the amount of lubricating agent is about 3 to about 5%.

23. The process of claim 1 wherein the division of the mixture is effected by a pump string-forming apparatus.

24. The process of claim 23 wherein the string-forming apparatus comprises a single- or multihole die plate having orifices with cross-section of about 0.5 to about 3 mm.

25. The process of claim 24 wherein the orifices have cross-sections of about 0.7 to about 1.5 mm.

26. The process of claim 1 wherein the particles are coated with an the anti-caking agent is selected from the group consisting of corn starch, other starches, absorbing silica and talcum powder.

27. The process of claim 1 wherein the division of the mixture into particles is effected at about 40° C. to about 70° C.

28. Enzyme-containing particles prepared by the process of claim 1.

29. An enzyme-containing composition comprising an enzyme in dry or substantially dry form, about 20% to about 60% of a hydrophilic organic cohesive compatible with the enzyme selected from the group consisting of starch and cellulose derivatives, arabic gum, karaya gum and tragacanth, about 10% to about 60% of a building agent suitable for use in enzyme compositions, and an amount of a moisture regulating agent selected from the group consisting of polyols having 2 to 6 carbon atoms and 2 to 4 hydroxy groups attached to different carbon atoms sufficient to maintain a moisture content in the particles formed of from 5% to 15% at ordinary temperatures and ordinary relative humidities and a small amount of water.

30. In washing compositions containing about 4 to about 20% of detergent, about 35 to 55% of water-softening agent, and a filler and other usual components to make up 100%, the improvement comprising also containing enzyme-containing particles of claim 35 in an amount sufficient to make the activity of the final washing composition about 1,000 to about 3,000 DU/g.

31. A washing compositions of claim 30 containing proteolytic-enzyme-containing particles in an amount sufficient to make the activity of the final washing composition about 1,500 to about 2,500 DU/g.

32. A washing compositions of claim 30 which comprises about 6 to about 12% of detergent and about 40 to about 50% of a water-softening agent.

33. Enzyme-containing particles comprising an enzyme in dry or substantially dry form, about 20% to about 60% of a hydrophilic organic cohesive compatible with the enzyme selected from the group consisting of starch and cellulose derivatives arabic gum, karaya gum and tragacanth, about 10% to about 60% of a building agent suitable for use in enzyme compositions and an amount of a moisture regulating agent selected from the group consisting of polyols having 2 to 6 carbon atoms and 2 to 4 hydroxy groups attache to different carbon atoms sufficient to maintain a moisture content in the particles formed of from 5% to 15% at ordinary temperatures and ordinary relative humidities and a small amount of water.

* * * * *